United States Patent
Papac

(10) Patent No.: US 9,782,232 B1
(45) Date of Patent: Oct. 10, 2017

(54) AUTOMATED INTRAOCULAR PRESSURE TAMPONADE

(71) Applicant: NOVARTIS AG, Basel (CH)

(72) Inventor: Michael J. Papac, North Tustin, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/137,209

(22) Filed: Apr. 25, 2016

(51) Int. Cl.
*G06K 9/00* (2006.01)
*A61B 90/00* (2016.01)
*A61F 9/007* (2006.01)
*A61B 17/00* (2006.01)

(52) U.S. Cl.
CPC .............. *A61B 90/03* (2016.02); *A61B 90/06* (2016.02); *A61B 90/361* (2016.02); *A61F 9/00736* (2013.01); *A61B 2017/00022* (2013.01); *A61B 2090/032* (2016.02); *A61B 2090/064* (2016.02); *A61B 2090/364* (2016.02); *A61B 2090/3612* (2016.02); *A61B 2505/05* (2013.01); *A61B 2560/0266* (2013.01); *A61B 2562/0247* (2013.01)

(58) Field of Classification Search
None
See application file for complete search history.

(56) References Cited

U.S. PATENT DOCUMENTS 8,430,840 B2 * 4/2013 Nazarifar ............ A61M 3/0233
604/246
8,903,475 B2 * 12/2014 Brennan .............. A61B 5/0066
356/246
8,903,476 B2 * 12/2014 Brennan .............. A61B 5/0066
356/246
2001/0014788 A1 8/2001 Morris
2002/0019607 A1 * 2/2002 Bui ..................... A61M 1/0058
604/67

(Continued)

OTHER PUBLICATIONS

Reimann and Miller, "True" IOP Control: A Constellation vision system Advanced Technology, Date: Nov. 11, 2009, Available online at: www.visioncareprofessional.com/emails/alcon/18/constellation_iop_advert.pdf.*

(Continued)

*Primary Examiner* — Tahmina Ansari
(74) *Attorney, Agent, or Firm* — S. Brannon Latimer

(57) ABSTRACT

An ophthalmic surgical system includes an imaging device configured to acquire a first image of a fundus of an eye and a hemorrhage detecting unit. The hemorrhage detecting unit includes a processor configured to receive the first fundus image from the imaging device, analyze the first fundus image to detect a hemorrhage in the eye, and in response to detecting the hemorrhage, send a signal to an intraocular pressure controller. The ophthalmic surgical system further includes the intraocular pressure controller, which includes a processor configured to receive the signal from the hemorrhage detecting unit, in response to the received signal, determine if a current intraoperative pressure of the eye is below a predetermined threshold, and in response to determining the current intraoperative pressure of the eye is below the predetermined threshold, generate a signal to increase the intraoperative pressure of the eye.

20 Claims, 6 Drawing Sheets

(56) References Cited

U.S. PATENT DOCUMENTS

2010/0029663 A1* 2/2010 Horn .................. A61K 9/08
 514/249
2011/0288475 A1 11/2011 Charles
2015/0031993 A1 1/2015 Buckland et al.
2015/0335484 A1 11/2015 Boukhny et al.

OTHER PUBLICATIONS

Packo, Kirk, True IOP control and Infusion Cannula Fluidics with the Constellation Vision System, Date: Oct. 1, 2010, Available online: www.retinalphysician.com/articleviePwer.aspx?articleid=104861.*

Packo, Kirk H., "True IOP Control and Infusion Cannula Fluidics with the Constellation Vision System," Oct. 1, 2010, available at: http://www.retinalphysician.com/articleviewer.aspx?articleID=104861.

Riemann, Christopher D. and Miller, Daniel M., "True IOP Control: A Constellation Vision System Advanced Technology," Nov. 11, 2009, available at: http://www.visioncareprofessional.com/emails/alcon/18/Constellation_IOP_advert.pdf.

* cited by examiner

AUTOMATED INTRAOCULAR PRESSURE TAMPONADE

FIELD

This present disclosure relates generally to ophthalmic surgery, and, more particularly, systems and methods for addressing hemorrhaging during ophthalmic surgery.

BACKGROUND

Posterior-segment surgical procedures include a variety of ophthalmic surgical procedures performed to treat conditions of the back of the eye, such as age-related macular degeneration (AMD), diabetic retinopathy and diabetic vitreous hemorrhage, macular hole, retinal detachment, epiretinal membrane, CMV retinitis, and others.

The vitreous is a normally clear, gel-like substance that fills the center of the eye. It makes up approximately two-thirds of the eye's volume, giving it form and shape. Certain problems affecting the back of the eye may require a vitrectomy, or surgical removal of the vitreous.

A vitrectomy may be performed to clear blood and debris from the eye, to remove scar tissue, or to alleviate traction on the retina. Blood, inflammatory cells, debris, and scar tissue obscure light as it passes through the eye to the retina, resulting in blurred vision. The vitreous is also removed if it is pulling or tugging the retina from its normal position. Some of the most common eye conditions that require vitrectomy include complications from diabetic retinopathy such as retinal detachment or bleeding, macular hole, retinal detachment, pre-retinal membrane fibrosis, bleeding inside the eye (vitreous hemorrhage), injury or infection, and certain problems related to previous eye surgery.

In a typical vitrectomy, a surgeon creates three tiny incisions in the eye for three separate instruments. These incisions are placed in the pars plana of the eye, which is located just behind the iris but in front of the retina. The instruments which pass through these incisions include a light pipe, an infusion port, and a vitrectomy cutting device.

The vitrector, or cutting device, works like a tiny guillotine, with an oscillating microscopic cutter to aspirate vitreous gel in a controlled fashion. As vitreous fluid is aspirated during posterior segment surgery, intraocular pressure drops and the eye tends to soften. The infusion port is thus used to infuse fluid (liquid and/or gas) in the eye to maintain intraocular pressure and avoid globe deformation or collapse. In addition, controlling intraocular pressure may help maintain scleral rigidity to facilitate movement of the eye and exchange of instruments during the procedure. Controlling intraocular pressure may also increase the visibility of eye tissues and reduce bleeding. However, intraocular pressure must be carefully regulated, as prolonged periods of elevated intraocular pressure can damage eye structures.

Hemorrhaging is a common problem in posterior segment surgery. Typically, a surgeon must monitor for hemorrhaging during a procedure and, in the event hemorrhaging occurs, must pause the procedure and manually adjust controls of a surgical console (e.g., via a foot pedal) to increase intraocular pressure for a period of time. Increasing intraocular pressure in this manner causes the infused fluid to act as a tamponade, compressing the hemorrhaging wound and allowing blood to clot. Once the bleeding stops, the surgeon clears the blood from the vitreous cavity and resumes the procedure.

In many cases, a surgeon may not recognize hemorrhaging until it reaches a point that blood obstructs the surgical view. This late recognition of hemorrhaging creates a situation that is dangerous for the patient, and consumes additional time in the surgical theater. Moreover, constantly monitoring for hemorrhaging is difficult and distracting for surgeon. Thus, there exists a need for improved systems and techniques to identify and respond to hemorrhaging as early as possible.

SUMMARY

According to certain embodiments of the present disclosure, an ophthalmic surgical system includes an imaging device configured to acquire a first image of a fundus of an eye. The system includes a hemorrhage detecting unit, which includes a processor configured to receive the first fundus image from the imaging device, analyze the first fundus image to detect a hemorrhage in the eye; and in response to detecting the hemorrhage, send a signal to an intraocular pressure controller. The system further includes the intraocular pressure controller, which includes a processor configured to receive the signal from the hemorrhage detecting unit, in response to the received signal, determine if a current intraoperative pressure of the eye is below a predetermined threshold, and in response to determining the current intraoperative pressure of the eye is below the predetermined threshold, generate a signal to increase the intraoperative pressure of the eye.

In certain embodiments, the processor of the intraocular pressure controller is further configured to, prior to generating a signal to increase the intraoperative pressure of the eye, determine if automatic increase of intraoperative pressure has been enabled. In response to determining that automatic increase of intraoperative pressure has not been enabled, the processor may request permission to increase intraoperative pressure.

According to certain embodiments, the processor of the intraocular pressure controller is further configured to, in response to determining the current intraoperative pressure of the eye is below the predetermined threshold, start a timer, and, in response to an expiration of the timer, generate a signal to decrease the intraoperative pressure of the eye. The processor of the intraocular pressure controller may be configured to, in response to determining the current intraoperative pressure of the eye is below the predetermined threshold, generate the signal to increase the intraoperative pressure of the eye to a pressure above 40 mmHg, and in response to the expiration of the timer, generate the signal to decrease the intraoperative pressure of the eye.

In certain embodiments, the processor of the intraocular pressure controller is further configured to generate an audio or visual alert to notify a system operator if the intraocular pressure controller determines that the current intraoperative pressure of the eye is not below the predetermined threshold.

In certain embodiments, the processor of the hemorrhage detecting unit may be configured to analyze the first fundus image using a machine vision algorithm.

In certain embodiments, the processor of the hemorrhage detecting unit is configured to analyze the first fundus image to detect a hemorrhage in the eye by identifying a first plurality of blood vessels in the first fundus image, comparing the first plurality of blood vessels in the first fundus image with a second plurality of blood vessels identified in a second fundus image, wherein the second fundus image is acquired prior to the fundus image, and wherein the first plurality of blood vessels and the second plurality of blood vessels are located in a particular region of the eye, and determining that the first plurality of blood vessels is larger than the second plurality of blood vessels.

According to particular embodiments, the processor of the hemorrhage detecting unit is configured to analyze the first fundus image to detect a hemorrhage in the eye by identifying a first contrast pattern in the first fundus image, comparing the first contrast pattern in the first fundus image with a second contrast pattern in a second fundus image, wherein the second fundus image was acquired prior to the fundus image, and wherein the first contrast pattern and the second contrast pattern correspond to a particular region of the eye, and determining that the first contrast pattern is larger than the second contrast pattern.

In certain embodiments, the imaging device is at least one of a digital video camera, line scan ophthalmoscope, or a confocal-scanning ophthalmoscope. In certain embodiments, the imaging device may be a multispectral imaging system or an optical coherence tomography (OCT) imaging system.

In certain embodiments, the hemorrhage detecting unit and the intraocular pressure controller are housed in a surgical console. The hemorrhage detecting unit and the intraocular pressure controller may be integrated.

Certain embodiments provide a method that includes acquiring a first image of a fundus of an eye, analyzing the first fundus image to detect a hemorrhage in the eye, in response to detecting the hemorrhage, determining if a current intraoperative pressure of the eye is below a predetermined threshold, and in response to determining the current intraoperative pressure of the eye is below the predetermined threshold, generating a signal to increase the intraoperative pressure of the eye.

The method may further include, in response to determining the current intraoperative pressure of the eye is below the predetermined threshold, starting a timer, and in response to an expiration of the timer, generating a signal to decrease the intraoperative pressure of the eye.

In certain embodiments, the method includes, in response to determining the current intraoperative pressure of the eye is below the predetermined threshold, generate the signal to increase the intraoperative pressure of the eye to a pressure above 40 mmHg, and in response to the expiration of the timer, generate the signal to decrease the intraoperative pressure of the eye.

Methods according to particular embodiments include generating an audio or visual alert to notify a system operator if the intraocular pressure controller determines that the current intraoperative pressure of the eye is not below the predetermined threshold.

In certain embodiments, the first fundus image is analyzed using a machine vision algorithm.

In certain embodiments, the first fundus image is analyzed to detect a hemorrhage in the eye by identifying a first plurality of blood vessels in the first fundus image, comparing the first plurality of blood vessels in the first fundus image with a second plurality of blood vessels identified in a second fundus image, wherein the second fundus image is acquired prior to the fundus image, and wherein the first plurality of blood vessels and the second plurality of blood vessels are located in a particular region of the eye, and determining that the first plurality of blood vessels is larger than the second plurality of blood vessels.

In certain embodiments, the first fundus image is analyzed to detect a hemorrhage in the eye by identifying a first contrast pattern in the first fundus image; comparing the first contrast pattern in the first fundus image with a second contrast pattern in a second fundus image, wherein the second fundus image was acquired prior to the fundus image, and wherein the first contrast pattern and the second contrast pattern correspond to a particular region of the eye, and determining that the first contrast pattern is larger than the second contrast pattern.

Certain embodiments of the present disclosure may provide one or more technical advantages. For example, embodiments of the present disclosure facilitate faster and more accurate detection and of and response to hemorrhaging that occurs during ophthalmic surgery. By detecting and responding to a hemorrhage more quickly, certain embodiments may provide an automated intraocular pressure tamponade to stop bleeding before it obscures the surgeon's surgical view, thereby improving patient safety. Further, as particular embodiments minimize bleeding by rapidly responding to hemorrhaging, they help a surgeon to clear the surgical area more quickly and reduce time spent in the surgical theater, saving time and expense. Automating the detection of hemorrhaging also facilitates improved patient outcomes by allowing a surgeon to focus on the surgical tools during a procedure, rather than checking for and investigating potential hemorrhaging.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

Figure 1A:
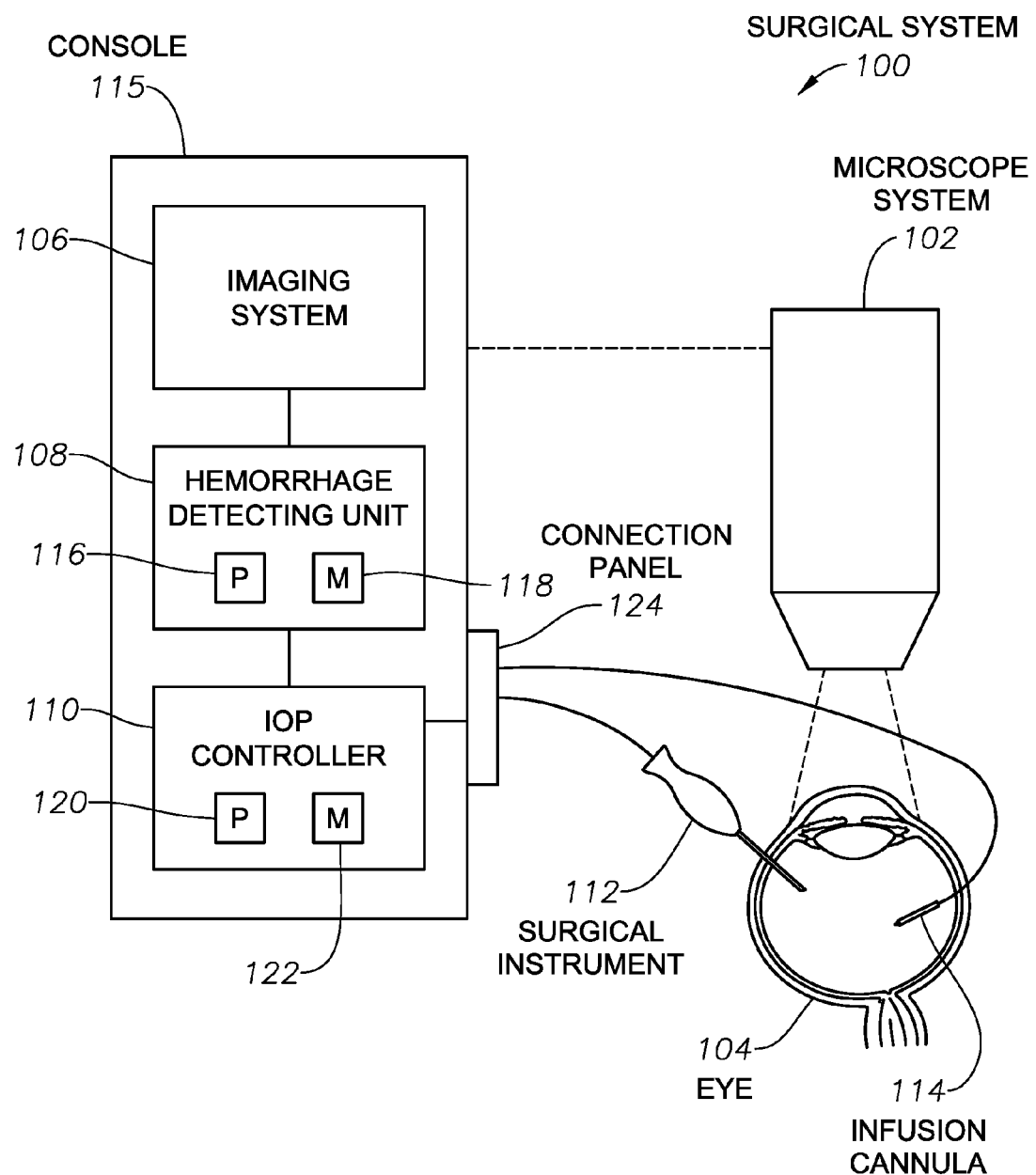
FIGS. 1A-1C illustrate surgical systems that provide an automated intraocular pressure tamponade, according to certain embodiments.

The skilled person in the art will understand that the drawings, described below, are for illustration purposes only. The drawings are not intended to limit the scope of the applicant's disclosure in any way.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in many instances the same reference numbers are used throughout the drawings to refer to the same or like parts.

In general, the present disclosure relates to systems and methods for providing an automated intraocular pressure tamponade for ophthalmic surgery. Certain embodiments provide a surgical system that includes an imaging system, hemorrhage detecting unit, and intraocular pressure controller that work together to automatically identify and respond to hemorrhaging during an ophthalmic surgical procedure. The disclosed surgical system may acquire and analyze fundus images in real time to monitor changes to blood vessels or other characteristics of the eye that indicate hemorrhaging. If hemorrhaging is detected, the disclosed system may automatically alert the surgeon and elevate intraocular pressure to compress the hemorrhaging wound until the blood clots. After set period of time, or after the system determines that the blood has sufficiently clotted, the surgical system may automatically lower intraocular pressure to a set point so that the procedure may safely continue.

Figure 1B:
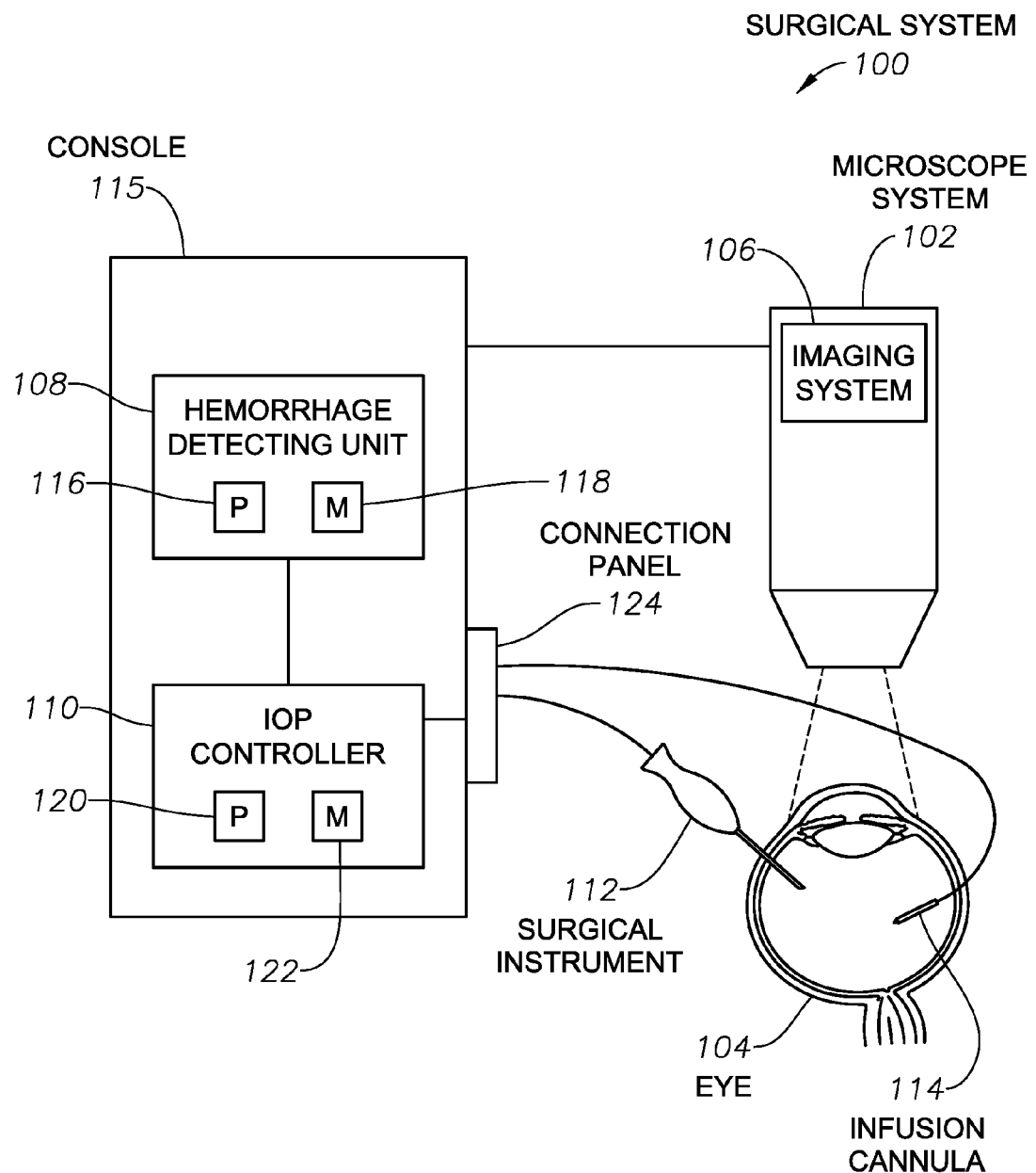
Figure 1C:
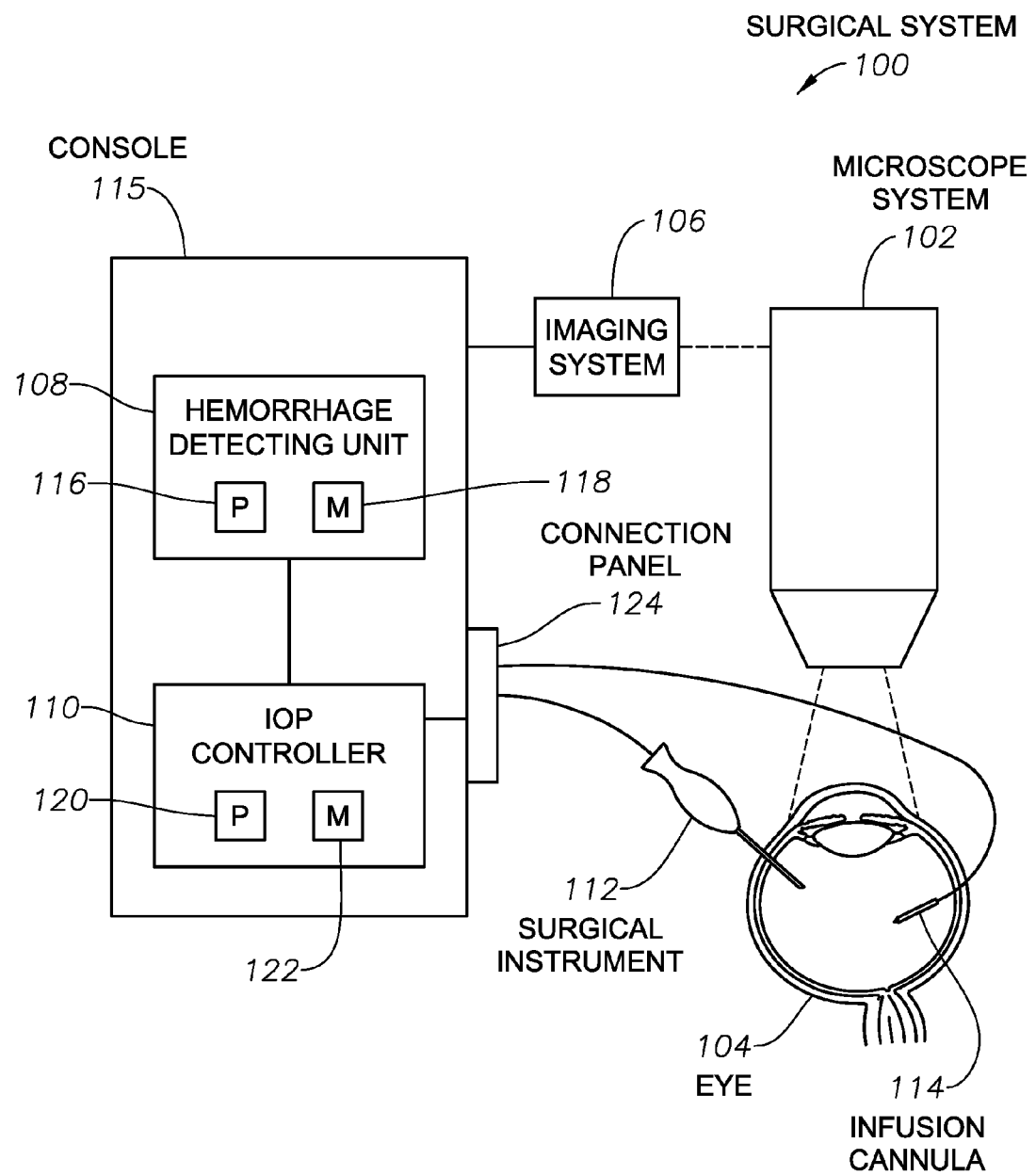

FIG. 1A illustrates a surgical system 100 according to certain embodiments. Surgical system 100 includes a surgical microscope 102 communicatively coupled to surgical console 115 for communicating images of eye 104. Surgical console 115 may include imaging system 106, hemorrhage detecting unit 108, intraocular pressure controller 110, and connection panel 124, each of which are communicatively coupled. As shown in FIG. 1A, imaging system 106, hemorrhage detecting unit 108, and/or intraocular pressure controller 110 may be integrated or may be discrete modular components within surgical console 115. As shown in FIG. 1B, in certain embodiments imaging system 106 may be located in or integrated with microscope system 102. As shown in FIG. 1C, in certain embodiments imaging system 106 may be a discrete component separate from microscope system 102 and surgical console 115.

Surgical console 115 includes a connection panel 124 used to connect various tools and consumables, such as surgical instrument 112 and infusion cannula 114, to surgical console 115. Surgical console 115 may be a standalone console, or may be integrated into a microscope scan. Surgical console 115 may be suitable for anterior or posterior ophthalmic surgery. One example of a surgical console 115 that may be adapted according to the present disclosure is the CONSTELLATION® Vision System available from Alcon Laboratories. As described more fully below, components of surgical system 100 collectively operate to provide an automated intraocular pressure tamponade to control hemorrhaging within eye 104 during a surgical procedure.

Microscope system 102 may acquire images of a patient's eye 104 using light in the visible or invisible spectrum. The visible spectrum defines the wavelength range of light that is visible to the human eye. The visible spectrum includes electromagnetic radiation having a wavelength that is generally within a range of about 400 nm to 700 nm, though this wavelength range may vary somewhat for different individuals. Microscope system 102 may use a system of lenses to provide a magnified view of eye 104 or a specific region of interest within eye 104. Microscope system 102 generally includes eyepieces, a relay lens, magnifying/focusing optics, an objective lens, and surgical viewing optics (not shown). Microscope system 102 may include any suitable optical components as understood by persons of ordinary skill in the art.

Microscope system 102 may be communicatively coupled (via wireless or wired communication) to surgical console 115 and/or imaging system 106. Light (including but not limited to light in the visible, near-visible, or infrared spectrum) reflected by a patient's eye 104 along the optical path of microscope 102 may be directed toward imaging system 106 via a mirror (not shown) placed along an optical path and operable to at least partially reflect light. Images and image data acquired by microscope system 102 may be communicated to imaging system 106 in any suitable manner.

Imaging system 106 may be any suitable device for generating a fundus image of eye 104 and may include suitable magnification and focusing optics for performing that function. Imaging system 106 may comprise a camera for acquiring discrete still photographs of eye 104 and/or a video camera for acquiring a continuous video stream of eye 104. In certain embodiments, imaging system 106 may include a line scan ophthalmoscope or confocal scanning ophthalmoscope. Imaging system 106 may comprise a multispectral imaging system, an infrared imaging system, or any other suitable imaging system.

In certain embodiments, imaging system 106 may include an optical coherence tomography (OCT) imaging system. OCT imaging systems may enable visualization of target tissue in depth by focusing a laser beam onto the garget, collecting the reflected beam, interfering the reflected beam with a reference beam and detecting the interference, and measuring the reflectance signature with the depth of focus of the beam. The result is a line scan in depth, a cross-sectional scan, or a volumetric scan. In certain embodiments, an OCT imaging system may generate live OCT images in real time during a surgical procedure.

Imaging system 106 may be a housed within surgical console 115, or may be a separate unit coupled to surgical console 115. Imaging system 106 may be housed within, integrated with, or attached to microscope system 102. As shown in FIG. 1A, in certain embodiments imaging system 106 may be a component of surgical console 115. As shown in FIG. 1B, in certain embodiments imaging system 106 may be integrated with microscope system 102. For example, imaging system 106 may be located in the head of a microscope of microscope system 102. As shown in FIG. 1C, in certain embodiments imaging system 106 may be a separate from microscope system 102 and surgical console 115.

In certain embodiments, imaging system 106 may be directly or indirectly coupled (via wired or wireless communication) to surgical console 115 and/or hemorrhage detecting unit 108, which receives images of eye 104 from imaging system 106. Images received from imaging system 106 may be discrete photographs or frames of a video stream.

Hemorrhage detecting unit 108 is operable to analyze images received from imaging system 106 and identify hemorrhaging or bleeding in eye 104 based on the images.

Hemorrhage detecting unit 108 may include any suitable combination of hardware, firmware, and software. In certain embodiments, hemorrhage detecting unit 108 may include processor 116 and memory 118. Processor 116 may include one or more microprocessors, field-programmable gate arrays (FPGAs), controllers, or any other suitable computing devices or resources. Processor 116 may work, either alone or with other components depicted in FIG. 1, to provide the functionality described herein. In certain embodiments, hemorrhage detecting unit 108, intraocular pressure controller 110, and/or other components of console 115 may be executed by a single processor or group of processors operating together. Memory 118 may take the form of volatile or non-volatile memory including, without limitation, magnetic media, optical media, random access memory (RAM), read-only memory (ROM), removable media, or any other suitable memory component. Memory 118 may store instructions for programs and algorithms that, when executed by processor 116, implement the functionality of hemorrhage detecting unit 108. Hemorrhage detecting unit 108 may be programmed to (or may store software in memory 118 that, when executed by processor 116, is operable to) analyze images received from imaging system 106 (e.g., fundus images) in order to determine if hemorrhaging or bleeding is present in eye 104.

Hemorrhage detecting unit 108 may use any suitable image-based processing techniques to analyze the images received from imaging system 106. By way of example, hemorrhage detecting unit 108 may analyze the images by employing machine vision or computer vision algorithms to identify and extract individual blood vessels, blood vessel patterns, or other high-contrast features in a plurality of photographs or video frames received from imaging system 106. Hemorrhage detecting unit 108 may use motion-based object tracking algorithms, such as background substraction, frame difference, or optical flow, to analyze images received from imaging system 106. Hemorrhage detecting unit 108 may use region-based or feature-based object tracking techniques, such as edge detection, corner detection, blob detection, blob extraction, ridge detection, scale-invariant feature transform, motion detection, optical flow, thresholding, template matching, or Hough transform, to analyze images received from imaging system 106.

In certain embodiments, hemorrhage detecting unit 108 may perform contrast and feature enhancement processing on images received from imaging system 106. In certain embodiments, hemorrhage detecting unit 108 may receive an image in Red-Green-Blue (RGB) format and convert the RGB image into a Hue-Saturation-Value (HSV) space. Hemorrhage detecting unit 108 may determine a first-order estimation mask of particular features in the image, such as one or more blood vessels or blood vessel patterns. Based on known contrast features of a blood vessel, hemorrhage detecting unit 108 may apply criteria to hue and saturation channels of an HSV image to separate the vessel from a background, in order to bring out and estimate the image of the blood vessel. Hemorrhage detecting unit 108 may extract the image of the blood vessels or blood vessel patterns, identify their position in the image, and utilize a blob-detection process to detect boundaries of the blood vessel(s) by searching for regions of approximately constant properties in the image frame.

Hemorrhage detecting unit 108 may continuously and quickly analyze multiple images received from imaging system 106 (e.g., frames of a real time video stream or photographs acquired over a period of time), and may compare the analysis of multiple images to identify changes that indicate or are consistent with hemorrhaging. For example, hemorrhage detecting unit 108 may compare the appearance of particular blood vessels or blood vessel patterns in a series of images acquired during a procedure in real time. Alternatively, hemorrhage detecting unit 108 may compare the appearance of particular blood vessels or blood vessel patterns in a real-time image (or series of images) acquired during a procedure with those in a reference image acquired at the beginning of or before the procedure. If hemorrhage detecting unit 108 determines, based on a comparison of analyzed images, that the blood vessels or blood vessel patterns appear to be swelling or increasing in size, it may send a signal to intraocular pressure controller 110 indicating that hemorrhaging has been detected.

Intraocular pressure controller 110 is communicatively coupled (via wired or wireless communication) to hemorrhaging detecting unit 108 and connection panel 124 to adjust and control intraocular pressure in eye 104. In certain embodiments, intraocular pressure controller 110 may be a component of connection panel 124.

Intraocular pressure controller 110 may include any suitable combination of hardware, firmware, and software. In certain embodiments, intraocular pressure controller 110 may include processor 120 and memory 122. Processor 120 may include one or more microprocessors, field-programmable gate arrays (FPGAs), controllers, or any other suitable computing devices or resources. Processor 120 may work, either alone or with other components depicted in FIG. 1, to provide the functionality described herein. In certain embodiments, intraocular pressure controller 110, hemorrhage detecting unit 108, and/or other components of console 115 may be executed by a single processor or group of processors operating together. Memory 122 may take the form of volatile or non-volatile memory including, without limitation, magnetic media, optical media, random access memory (RAM), read-only memory (ROM), removable media, or any other suitable memory component.

Memory 122 may store instructions for programs and algorithms that, when executed by processor 120, implement the functionality of intraocular pressure controller 110. Intraocular pressure controller 110 may be programmed to (or may store software in memory 122 that, when executed by processor 120, is operable to) monitor and adjust the intraocular pressure in eye 104 in response to signals received from hemorrhage detecting unit 108.

Connection panel 124 includes any suitable components for coupling to and supporting the operation of surgical instrument 112 and infusion cannula 114. In particular embodiments, connection panel 124 may include a surgical cassette receiver and a surgical cassette, such as a cassette for use with the CONSTELLATION® Vision System available from Alcon Laboratories. Connection panel 124 may be physically coupled to surgical instrument 112 and infusion cannula 114 via surgical tubing for infusion and/or aspiration of fluid or tissue. Connection panel 124 may be electronically coupled to surgical instrument 112, infusion cannula 114, and other tools via wired or wireless electrical connections. Connection panel 124, surgical instrument 112, and/or infusion cannula 114 may include one or more sensors for monitoring flow rate, pressure, and other conditions related to eye 114.

Surgical instrument 112 may comprise any tool for ophthalmic surgery, such as a vitrectomy probe. In certain embodiments, surgical instrument 112 includes a cutting blade and one or more ports to aspirate vitreous humor. In certain embodiments, surgical instrument 112 may comprise a CONSTELLATION® ULTRAVIT® Anterior Vitrectomy Probe available from Alcon Laboratories.

Infusion cannula 114 may include one or more ports suitable for injecting fluid (e.g., silicone oil, saline, water, gas) into eye 104. In certain embodiments, infusion cannula 114 may comprise an EDGEPLUS® Valved Trocar Cannula System available from Alcon Laboratories. In certain embodiments, surgical instrument 112 and infusion cannula 114 may be integrated.

In operation, a surgeon may set an intraocular pressure level for a procedure via a user interface or other input device of surgical console 115. For example, a surgeon may set intraocular pressure via a foot pedal, touchscreen, keyboard, mouse, voice command, or other input.

Intraocular pressure controller 110 then generates signals to control one or more valve(s), line(s), pump(s), actuator(s), and/or other mechanisms in surgical console 115, connection panel 124, surgical instrument 112, and/or infusion cannula 114 to increase, decrease, or maintain a particular intraocular pressure setting. In certain embodiments, intraocular pressure controller 110 is configured to receive signals from sensors (e.g., flow, pressure, and/or fluid level sensors) located in connection panel 124, surgical instrument 112, and/or infusion cannula 114. For example, intraocular pressure controller 110 may receive signals from one or more sensors embedded in a cassette of connection panel 124 to measure and predict intraocular pressure in eye 104 and infusion flow through infusion cannula 114. Intraocular pressure controller 110 may also calculate impedance data for components of system 100. For example, intraocular pressure controller 110 may calculate hydraulic resistance to fluid flow through system components (such as infusion tubing, a stopcock, and infusion cannula 114), and may calculate fluid dynamics for a range of infusion flow rates through those components.

Based on received sensor data and calculated data, intraocular pressure controller 110 may calculate a predicted intraocular pressure for particular conditions, and may compensate pressure to precisely control intraocular pressure at the tip of infusion cannula 114 in real time. In certain embodiments, as infusion fluid flows into eye 104, intraocular pressure controller 110 may automatically anticipate pressure drops and increase infusion pressure to match and compensate for the pressure drop across infusion cannula 114, thereby maintaining intraocular pressure within a consistent range.

In addition, intraocular pressure controller 110 is configured to increase or decrease intraocular pressure in response to signals received from hemorrhage detecting unit 108. For example, if hemorrhage detecting unit 108 determines that a hemorrhage is occurring based on an image analysis, it may send a signal indicating a hemorrhage to intraocular pressure controller 110. Intraocular pressure controller 110 may, in response to the signal, check the current intraocular pressure in eye 104. If the current intraocular pressure is not above a predetermined threshold (e.g., an upper bound of a normal intraocular pressure range), intraocular pressure controller 110 may notify a system operator that a hemorrhage has been detected and request confirmation to increase intraocular pressure by, for example, displaying a visual cue or making a sound to prompt a response from the surgeon. If an affirmative response is received from the surgeon (e.g., via a foot pedal, touchscreen, keyboard, or voice command), intraocular pressure controller 110 may increase the intraocular pressure in eye 104. In certain embodiments, a surgeon may control an automatic intraocular pressure response setting, such that when a hemorrhage is detected and the current intraocular pressure is not above a predetermined threshold, intraocular pressure 110 automatically increases the intraocular pressure in eye 104 without waiting for an affirmative response from the surgeon.

Elevated intraocular pressure may act as a tamponade to stop the bleeding in eye 104. In certain embodiments, intraocular pressure controller 110 may automatically reduce the intraocular pressure back to a preferred/normal level after a specified period of time. In other embodiments, imaging system 106 and hemorrhaging detecting unit 108 may receive and analyze additional images of eye 104 to determine whether blood at the hemorrhaging wound has clotted. If so, hemorrhage detecting unit may signal intraocular pressure controller 110 that the hemorrhage has ceased, and intraocular pressure controller 110 may reduce pressure back to a preferred/normal level, before a specified period of time has lapsed.

Accordingly, components of surgical system 100 provide an automated intraocular pressure tamponade to quickly detect and respond to hemorrhaging during ophthalmic surgery. In certain embodiments, hemorrhage detecting unit 108 and imaging system 106 continuously acquire and analyze real-time images obtained during a procedure and may detect hemorrhaging before it becomes visible to a surgeon. Accordingly, components of system 100 facilitate early hemorrhage detection, and allow the surgeon to focus on the procedure at hand without the distraction of observing blood vessels for hemorrhaging. Moreover, intraocular pressure controller 110 may automatically initiate measures to increase intraocular pressure in response to a detected hemorrhage, thereby minimizing bleeding to keep the surgical view clear. Accordingly, surgical system 100 facilitates improved patient safety and helps minimize time spent in the surgical theater, saving costs.

Figure 2A:
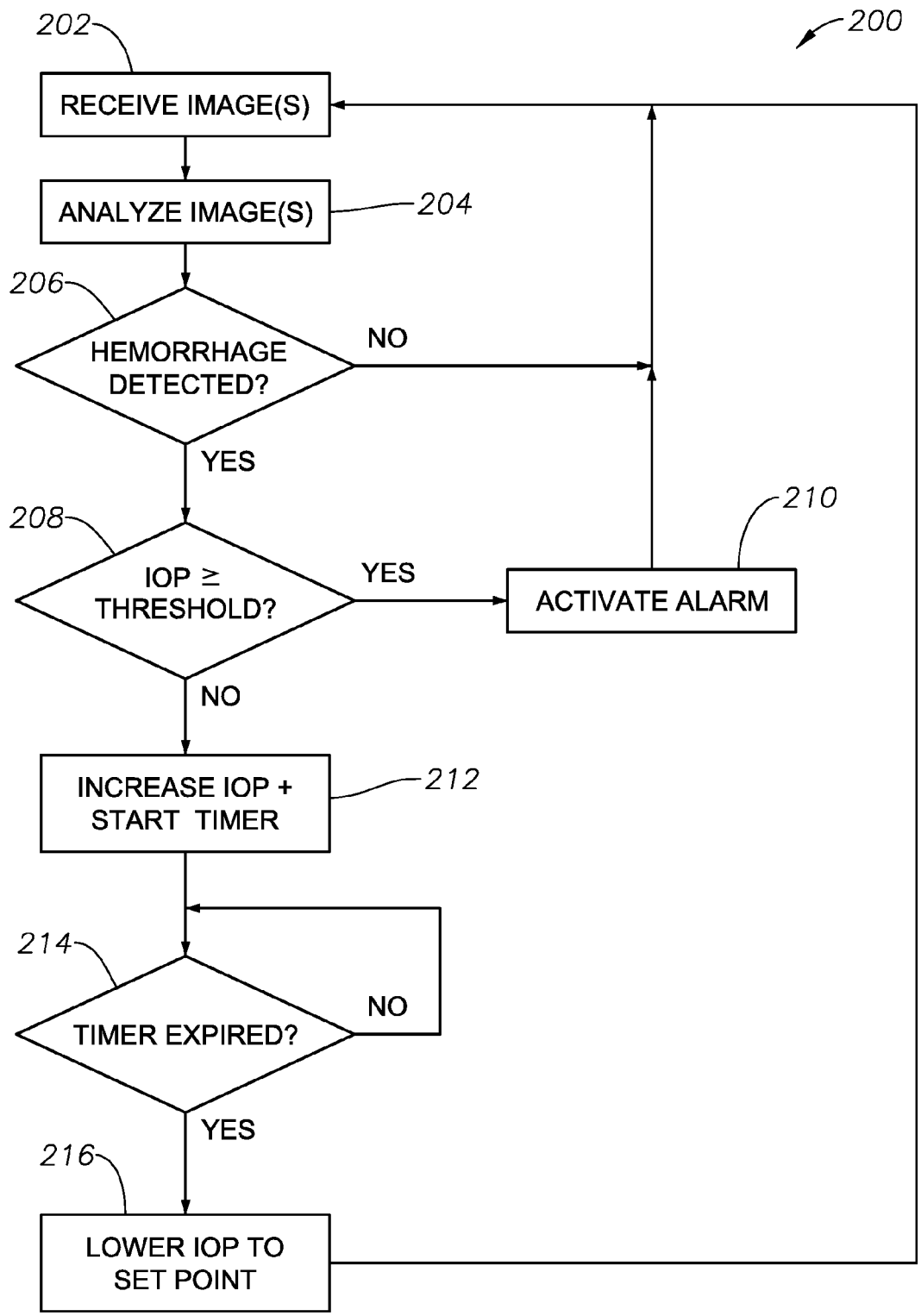
FIGS. 2A-2C illustrate methods for providing an automated intraocular pressure tamponade, according to certain embodiments.

FIG. 2A is a flow chart illustrating the operation of surgical system 100 to provide an intraocular pressure automated tamponade, according to certain embodiments.

At step 202, surgical system 100 receives one or more images of eye 104. The images may be acquired by imaging system 106, which receives the images from microscope system 102 via a mirror, beam splitter, or electronically. Images may be obtained during an ophthalmic surgical procedure, and may comprise one or more real-time photographs or video frames of a fundus image acquired by a surgical microscope. The images may be obtained by a digital video camera, a line scan ophthalmoscope, a confocal-scanning ophthalmoscope, a multispectral imaging system, an OCT imaging system, or any other suitable imaging system. A reference image may be obtained prior to or at the beginning of an ophthalmic surgical procedure, and images may be stored in memory of imaging system 106, or may be transmitted to hemorrhage detecting unit 108 and stored in associated memory 118.

At step 204, surgical system 100 analyzes the received images. In certain embodiments, imaging system 106 provides the images to hemorrhage detecting unit 108 for processing in real time. Hemorrhage detecting unit 108 may apply machine vision or computer vision imagine processing techniques to identify and extract blood vessels and/or blood vessel patterns within the received images. Extracted blood vessel and/or blood pattern image data may be stored in memory of tracking unit 108.

At step 206, surgical system 100 determines whether a hemorrhage has been detected. In certain embodiments, hemorrhage detecting unit 108 compares blood vessels and/or blood vessel patterns extracted from a first image with blood vessels and/or blood vessel patterns extracted from a reference image to identify any differences. Based on identified differences, hemorrhage detecting unit 108 may determine whether or not eye 104 is hemorrhaging. For example, if a comparison of analyzed images reveals that blood vessels in eye 104 have not changed, hemorrhaging detecting unit 108 may determine that a hemorrhage is not occurring. In that case, no hemorrhage is detected, and surgical system 100 returns to step 202. However, if a comparison of analyzed images reveals that blood vessels in eye 104 are becoming larger, hemorrhaging detecting unit 108 may detect a hemorrhage, and surgical system 100 proceeds to step 208.

At step 208, surgical system 100 checks the current intraocular pressure against a threshold intraocular pressure. In certain embodiments, when hemorrhage detecting unit 108 detects a hemorrhage, it sends a signal to intraocular pressure controller 110. In response to the signal indicating a hemorrhage, intraocular pressure controller 110 determines whether the current intraocular pressure in eye 104 is at or below a predetermined threshold. The predetermined threshold may be an upper limit of a normal intraocular pressure range. For example, if a normal intraocular pressure level during a surgical procedure is approximately 10-40 mmHg, intraocular pressure controller 110 may determine whether the current intraocular pressure is below 40 mmHg. It is to be understood that particular values discussed herein are not restrictive, but are provided as examples that do not limit the scope of the disclosure. In certain embodiments, the predetermined threshold may be a value in an elevated intraocular pressure range, such as 80-100 mmHg. The predetermined threshold may be configured by a surgeon prior to or during a surgical procedure to any suitable pressure level.

At step 210, if the intraocular pressure is above the threshold, intraocular pressure controller 110 may activate a notification or alarm to alert a system operator that a hemorrhage has been detected at a high intraocular pressure. If the intraocular pressure is below the threshold, intraocular pressure controller 110 may proceed to step 212. In certain embodiments, system 100 may notify the system operator that a hemorrhage has been detected and request permission to proceed to step 212.

At step 212, surgical system 100 increases the intraocular pressure and initiates a timer. In certain embodiments, intraocular pressure controller 110 increases intraocular pressure only in response to a positive confirmation obtained from a system operator. Intraocular pressure controller 110 may send signals to control valves, pumps, lines, actuators, and other mechanisms in surgical console 115, connection panel 124, surgical instrument 112, and/or infusion cannula 114 to increase intraocular pressure to a specified level. In certain embodiments, intraocular pressure is increased to between approximately 80-120 mmHg. In certain embodiments, intraocular pressure controller 110 may start a 1-5 minute timer when it increases intraocular pressure in response to a detected hemorrhage.

At step 214, surgical system 100 determines whether the timer has expired. In certain embodiments, intraocular pressure controller 110 monitors a countdown timer to determine if a preset amount of time has expired. If the timer has not expired, intraocular pressure controller 110 continues monitoring the timer at step 214. If the timer has expired, intraocular pressure controller 110 may proceed to step 216.

At step 216, surgical system 100 lowers the intraocular pressure of eye 104 to a set point. In certain embodiments, intraocular pressure controller 110 automatically lowers the intraocular pressure of eye 104 to a pressure level being maintained before the hemorrhage was detected at step 206. Alternatively, intraocular pressure controller 110 may lower the intraocular pressure of eye 104 to a different set point. In some embodiments, the set point is between 10-40 mmHg. Intraocular pressure controller may send signals to control valves, lines, actuators, and other mechanisms in connection panel 124, surgical instrument 112, and/or infusion cannula 114 to decrease intraocular pressure to a specified level.

Figure 2B:
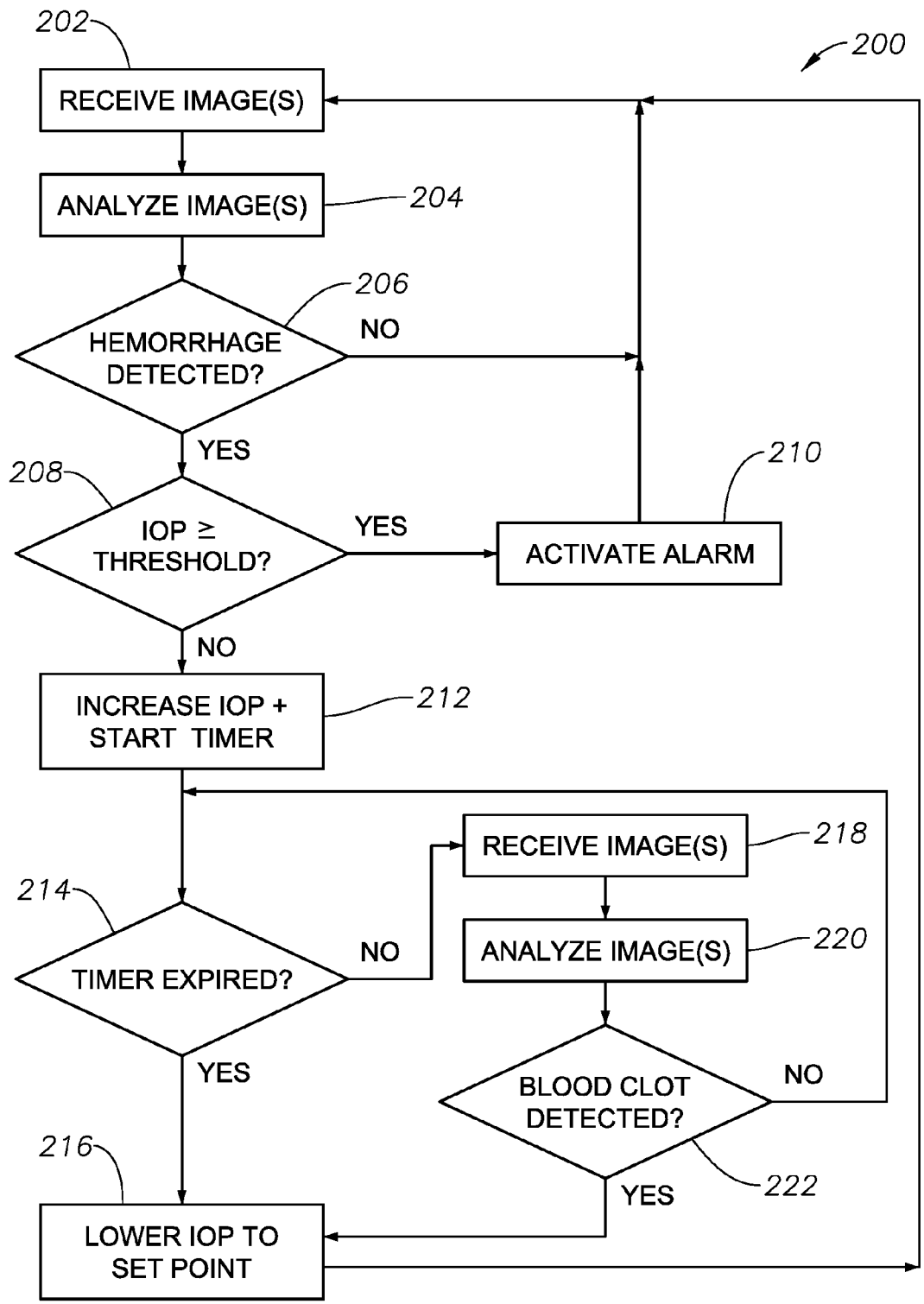

FIG. 2B is a flow chart illustrating the operation of surgical system 100 to provide an intraocular pressure automated tamponade, according to other embodiments. The flow chart of FIG. 2B is identical to FIG. 2A, except that it includes additional steps 218, 220, and 222.

As explained above with respect to FIG. 2A, at step 214, surgical system 100 determines whether the timer has expired. In certain embodiments, intraocular pressure controller 110 monitors a countdown timer to determine if a preset amount of time has expired. If the timer has expired, intraocular pressure controller 110 may proceed to step 216 and lower pressure to a set point.

In embodiments of FIG. 2B, if the timer has not expired at step 214, surgical system 100 proceeds to step 218 and may receive one or more updated images of eye 104, as described for step 202 above.

At step 220, surgical system 100 analyzes the updated images. In certain embodiments, imaging system 106 provides the images to hemorrhage detecting unit 108 for processing. As in step 204, hemorrhage detecting unit 108 may apply machine vision or computer vision imagine processing techniques to identify and extract blood vessels and/or blood vessel patterns within the received images. Extracted blood vessel and/or blood pattern image data may be stored in memory of tracking unit 108.

At step 222, surgical system 100 determines whether the blood at the hemorrhaging wound has clotted. In certain embodiments, hemorrhage detecting unit 108 compares blood vessels and/or blood vessel patterns extracted from one or more updated images with those extracted from one or more previous images (depicting hemorrhaging) to identify and monitor changes consistent with blood clotting. Based on changes and/or differences in the images, hemorrhage detecting unit 108 may determine whether the hemorrhaging wound has clotted sufficiently such that intraocular pressure may be lowered. If a comparison of analyzed images reveals that blood has not clotted in the wound, no blood clot is detected and surgical system 100 returns to step 214. However, if a comparison of analyzed images reveals that blood has sufficiently clotted in the wound, a blood clot is detected and surgical system 216 may proceed to lower intraocular pressure to a set point at step 216, even before expiration of the timer.

Figure 2C:
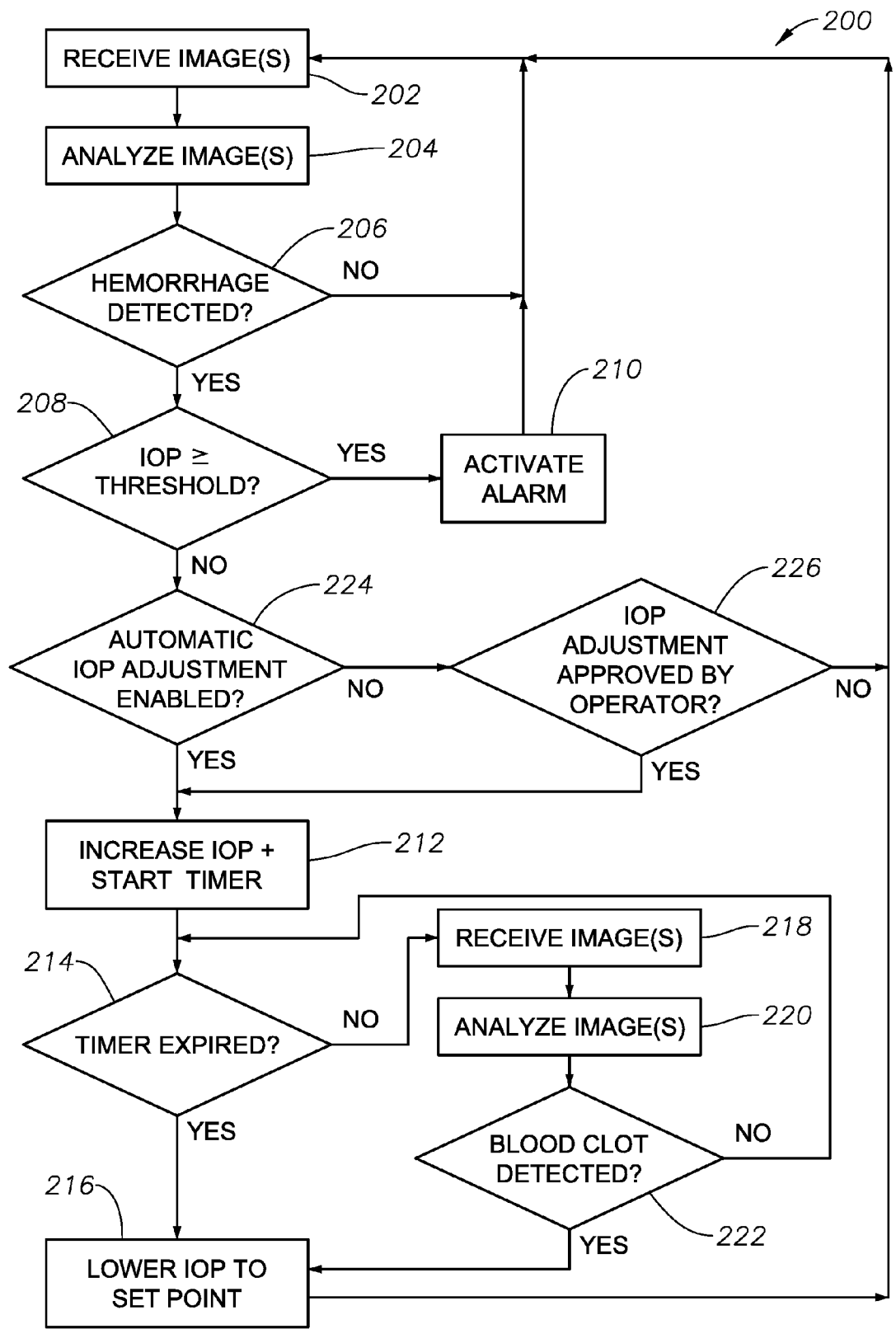

FIG. 2C is a flow chart illustrating the operation of surgical system 100 to provide an intraocular pressure automated tamponade, according to other embodiments. The flow chart of FIG. 2C is identical to FIG. 2B, except that it includes additional steps 224 and 226.

As explained above, at step 208 surgical system 100 checks the current intraocular pressure against a threshold intraocular pressure. If the intraocular pressure does not exceed the threshold, surgical system 100 may check at step 224 whether automatic adjustment of intraocular pressure has been enabled. In certain embodiments, intraocular pressure controller 110 determines if a system operator has specified that intraocular pressure may be adjusted automatically in the event a hemorrhage is detected. Certain embodiments provide a configurable setting (e.g., a soft key, hard key, menu option, etc.) that allows an operator to specify or configure permissions or settings to control whether intraocular pressure may be automatically increased in response to positive results at step 206 and step 208, without first obtaining manual verification/permission from an operator at the time the hemorrhage is detected. If so, surgical system 100 proceeds to step 212, as described above.

If the result at step 224 is negative, surgical system 100 proceeds to step 226. In certain embodiments, intraocular pressure controller 110 requests permission from a system operator before increasing intraocular pressure. In certain embodiments, intraocular pressure controller 110 sends a signal to cause another component of system 100 (e.g., a display or speaker) to present an audio and/or visual alert informing an operator that a hemorrhage has been detected. Intraocular pressure controller 110 may then await a response from the operator indicating that intraocular pressure may be increased. The operator may, for example, approve or permit adjustment of intraocular pressure by making an appropriate selection or input via a foot pedal, touchscreen, keyboard, mouse, voice command, or other interface. If intraocular pressure controller 110 receives approval/permission from the operator to adjust intraocular pressure, system 100 proceeds to step 212 as described above. If, however, the operator does not approve adjustment of intraocular pressure, system 100 returns to step 202.

It is expressly noted that features or steps described with respect to any of FIGS. 2A-2C may be combined in any manner, according to various embodiments. For example, the embodiments of FIG. 2A may be modified to include steps 224 and 226 of FIG. 2C.

It will be appreciated that several of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. An ophthalmic surgical system, comprising:
    an imaging device configured to acquire a first image of a fundus of an eye;
    a hemorrhage detecting unit comprising a processor configured to:
        receive the first fundus image from the imaging device;
        analyze the first fundus image to detect a hemorrhage in the eye; and
        in response to detecting the hemorrhage, send a signal to an intraocular pressure controller;
    the intraocular pressure controller comprising a processor configured to:
        receive the signal from the hemorrhage detecting unit;
        in response to the received signal, determine if a current intraoperative pressure of the eye is below a predetermined threshold; and
        in response to determining the current intraoperative pressure of the eye is below the predetermined threshold, generate a signal to increase the intraoperative pressure of the eye.

2. The ophthalmic surgical system of claim 1, wherein the processor of the intraocular pressure controller is further configured to:
    prior to generating a signal to increase the intraoperative pressure of the eye, determine if automatic increase of intraoperative pressure has been enabled;
    in response to determining that automatic increase of intraoperative pressure has not been enabled, requesting permission to increase intraoperative pressure.

3. The ophthalmic surgical system of claim 1, wherein the processor of the intraocular pressure controller is further configured to:
    in response to determining the current intraoperative pressure of the eye is below the predetermined threshold, start a timer; and
    in response to an expiration of the timer, generate a signal to decrease the intraoperative pressure of the eye.

4. The ophthalmic surgical system of claim 3, wherein the processor of the intraocular pressure controller is further configured to:
    in response to determining the current intraoperative pressure of the eye is below the predetermined threshold, generate the signal to increase the intraoperative pressure of the eye to a pressure above 40 mmHg; and
    in response to the expiration of the timer, generate the signal to decrease the intraoperative pressure of the eye.

5. The ophthalmic surgical system of claim 1, wherein the processor of the intraocular pressure controller is further configured to:
    generate an audio or visual alert to notify a system operator if the intraocular pressure controller determines that the current intraoperative pressure of the eye is not below the predetermined threshold.

6. The ophthalmic surgical system of claim 1, wherein the processor of the hemorrhage detecting unit is configured to analyze the first fundus image using a machine vision algorithm.

7. The ophthalmic surgical system of claim 1, wherein the processor of the hemorrhage detecting unit is configured to analyze the first fundus image to detect a hemorrhage in the eye by:
    identifying a first plurality of blood vessels in the first fundus image;
    comparing the first plurality of blood vessels in the first fundus image with a second plurality of blood vessels identified in a second fundus image, wherein the second fundus image is acquired prior to the fundus image, and wherein the first plurality of blood vessels and the second plurality of blood vessels are located in a particular region of the eye; and
    determining that the first plurality of blood vessels is larger than the second plurality of blood vessels.

8. The ophthalmic surgical system of claim 1, wherein the processor of the hemorrhage detecting unit is configured to analyze the first fundus image to detect a hemorrhage in the eye by:
    identifying a first contrast pattern in the first fundus image;
    comparing the first contrast pattern in the first fundus image with a second contrast pattern in a second fundus image, wherein the second fundus image was acquired prior to the fundus image, and wherein the first contrast pattern and the second contrast pattern correspond to a particular region of the eye; and
    determining that the first contrast pattern is larger than the second contrast pattern.

9. The ophthalmic surgical system of claim 1, wherein the imaging device is at least one of a digital video camera, line scan ophthalmoscope, or a confocal-scanning ophthalmoscope.

10. The ophthalmic surgical system of claim 1, wherein the imaging device is a multispectral imaging system.

11. The ophthalmic surgical system of claim 1, wherein the imaging device is an optical coherence tomography (OCT) imaging system.

12. The ophthalmic surgical system of claim 1, wherein the hemorrhage detecting unit and the intraocular pressure controller are housed in a surgical console.

13. The ophthalmic surgical system of claim 1, wherein the hemorrhage detecting unit and the intraocular pressure controller are integrated.

14. A method, comprising:
    acquiring a first image of a fundus of an eye;
    analyzing the first fundus image to detect a hemorrhage in the eye;
    in response to detecting the hemorrhage, determining if a current intraoperative pressure of the eye is below a predetermined threshold; and in response to determining the current intraoperative pressure of the eye is below the predetermined threshold, generating a signal to increase the intraoperative pressure of the eye.

15. The method of claim 14, further comprising: in response to determining the current intraoperative pressure of the eye is below the predetermined threshold, starting a timer; and in response to an expiration of the timer, generating a signal to decrease the intraoperative pressure of the eye.

16. The method of claim 15, further comprising: in response to determining the current intraoperative pressure of the eye is below the predetermined threshold, generate the signal to increase the intraoperative pressure of the eye to a pressure above 40 mmHg; and in response to the expiration of the timer, generate the signal to decrease the intraoperative pressure of the eye.

17. The method of claim 14, further comprising: generating an audio or visual alert to notify a system operator if the intraocular pressure controller determines that the current intraoperative pressure of the eye is not below the predetermined threshold.

18. The method of claim 14, wherein the first fundus image is analyzed using a machine vision algorithm.

19. The method of claim 14, wherein the first fundus image is analyzed to detect a hemorrhage in the eye by: identifying a first plurality of blood vessels in the first fundus image; comparing the first plurality of blood vessels in the first fundus image with a second plurality of blood vessels identified in a second fundus image, wherein the second fundus image is acquired prior to the fundus image, and wherein the first plurality of blood vessels and the second plurality of blood vessels are located in a particular region of the eye; and determining that the first plurality of blood vessels is larger than the second plurality of blood vessels.

20. The method of claim 14, wherein the first fundus image is analyzed to detect a hemorrhage in the eye by: identifying a first contrast pattern in the first fundus image; comparing the first contrast pattern in the first fundus image with a second contrast pattern in a second fundus image, wherein the second fundus image was acquired prior to the fundus image, and wherein the first contrast pattern and the second contrast pattern correspond to a particular region of the eye; and determining that the first contrast pattern is larger than the second contrast pattern.

* * * * *